US009099281B2

(12) United States Patent
Yaguchi et al.

(10) Patent No.: US 9,099,281 B2
(45) Date of Patent: Aug. 4, 2015

(54) CHARGED PARTICLE RADIATION APPARATUS, AND METHOD FOR DISPLAYING THREE-DIMENSIONAL INFORMATION IN CHARGED PARTICLE RADIATION APPARATUS

(75) Inventors: Toshie Yaguchi, Omitama (JP); Yasuhira Nagakubo, Hitachinaka (JP); Junzo Azuma, Hitachiota (JP); Akira Watabe, Higashiibaraki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 639 days.

(21) Appl. No.: 13/503,976

(22) PCT Filed: Oct. 22, 2010

(86) PCT No.: PCT/JP2010/068656
§ 371 (c)(1),
(2), (4) Date: Apr. 25, 2012

(87) PCT Pub. No.: WO2011/052489
PCT Pub. Date: May 5, 2011

(65) Prior Publication Data
US 2012/0212583 A1  Aug. 23, 2012

(30) Foreign Application Priority Data

Oct. 26, 2009  (JP) ................ 2009-245029

(51) Int. Cl.
*H04N 13/02* (2006.01)
*H01J 37/26* (2006.01)
(Continued)

(52) U.S. Cl.
CPC ............ *H01J 37/26* (2013.01); *G01N 23/2204* (2013.01); *G01N 23/2251* (2013.01);
(Continued)

(58) Field of Classification Search
CPC ...... G02B 21/365; G02B 21/06; G02B 21/26; G02B 21/008; G02B 21/0032; G02B 21/34; G02B 21/00; G06T 2207/10012; G06T 2207/10028; G06T 15/00; A61B 1/00193
USPC ............................................... 348/46, 79, 80
See application file for complete search history.

(56) References Cited

U.S. PATENT DOCUMENTS 5,036,205 A * 7/1991 Clement et al. .......... 250/442.11
5,753,924 A   5/1998 Swann
(Continued)

FOREIGN PATENT DOCUMENTS

JP  6-76777 A   3/1994
JP  6-349928 A  12/1994
(Continued)

OTHER PUBLICATIONS
European Search Report dated Nov. 7, 2013 (eleven (11) pages).
(Continued)

*Primary Examiner* — Andy Rao
*Assistant Examiner* — Jared Walker
(74) *Attorney, Agent, or Firm* — Crowell & Moring LLP

(57) ABSTRACT

Disclosed is a charged particle radiation apparatus capable of capturing a change in a sample due to gaseous atmosphere, light irradiation, heating or the like without exposing the sample to atmosphere. The present invention relates to a sample holder provided with a sample stage that is rotatable around a rotation axis perpendicular to an electron beam irradiation direction, the sample holder being capable of forming an airtight chamber around the sample stage. A sample is allowed to chemically react in any atmosphere, and three-dimensional analysis on the reaction is enabled. A sample liable to change in atmosphere can be three-dimensionally analyzed without exposing the sample to the atmosphere.

28 Claims, 11 Drawing Sheets

(51) Int. Cl.
  *G01N 23/22* (2006.01)
  *H01J 37/18* (2006.01)
  *H01J 37/20* (2006.01)
  *G01N 23/225* (2006.01)

(52) U.S. Cl.
  CPC ............... *H01J37/18* (2013.01); *H01J 37/20* (2013.01); *H01J 2237/006* (2013.01); *H01J 2237/2003* (2013.01); *H01J 2237/24578* (2013.01); *H01J 2237/2608* (2013.01); *H01J 2237/2611* (2013.01)

(56) References Cited

U.S. PATENT DOCUMENTS

| | | | |
|---|---|---|---|
| 6,410,925 | B1 | 6/2002 | Armbruster et al. |
| 7,053,370 | B2 | 5/2006 | Motoi et al. |
| 2004/0114806 | A1* | 6/2004 | Katayama et al. ............ 382/218 |
| 2005/0230636 | A1 | 10/2005 | Tanaka et al. |
| 2006/0202119 | A1* | 9/2006 | Yamada et al. ............... 250/310 |
| 2008/0093565 | A1 | 4/2008 | Yaguchi et al. |
| 2008/0265158 | A1* | 10/2008 | Iwasaki ......................... 250/310 |
| 2008/0290290 | A1 | 11/2008 | Nagakubo et al. |
| 2009/0127474 | A1* | 5/2009 | Tsuneta et al. ........... 250/442.11 |

FOREIGN PATENT DOCUMENTS

| | | |
|---|---|---|
| JP | 8-31361 A | 2/1996 |
| JP | 9-129168 A | 5/1997 |
| JP | 10-111223 A | 4/1998 |
| JP | 2000-215837 A | 8/2000 |
| JP | 2003-187735 A | 7/2003 |
| JP | 2004-87214 A | 3/2004 |
| JP | 2004-508661 A | 3/2004 |
| JP | 2005-148003 A | 6/2005 |
| JP | 2005-327710 A | 11/2005 |
| JP | 2007-172393 A | 7/2007 |
| JP | 2007-188905 A | 7/2007 |
| JP | 2008-108429 A | 5/2008 |
| JP | 2008-288161 A | 11/2008 |
| JP | 2009-117196 A | 5/2009 |
| JP | 2009-122122 A | 6/2009 |
| WO | WO 96/20495 A2 | 7/1996 |
| WO | WO 02/11174 A1 | 2/2002 |

OTHER PUBLICATIONS

Japanese-language Office Action dated May 7, 2013 (Two (2) pages).
International Search Report with English translation dated Dec. 28, 2010 (four (4) pages).
Form PCT/ISA/237 (five (5) pages), Dec. 28, 2010.

* cited by examiner

CHARGED PARTICLE RADIATION APPARATUS, AND METHOD FOR DISPLAYING THREE-DIMENSIONAL INFORMATION IN CHARGED PARTICLE RADIATION APPARATUS

TECHNICAL FIELD

The present invention relates to a sample holder used for electron microscopes and FIB processing apparatuses.

BACKGROUND ART

There is a growing need for observation of a three-dimensional structure that a sample originally has using a transmission electron microscope (TEM) and a scanning transmission electron microscope (STEM).

JP Patent Publication (Kokai) No. 2009-122122 A (Patent Document 1), for example, describes one of the observation methods of using a sample holder enabling 360-degree rotation of a sample to capture two-dimensional continuous projection images of the sample while rotating it and reconstructing a three-dimensional structure from the captured two-dimensional projection images. JP Patent Publication (Kokai) No. 2007-188905 A (Patent Document 2) describes a sample holder enabling processing and observation from any direction.

JP Patent Publication (Kokai) No. H06-349928 A (1994) (Patent Document 3) describes a sample conveyance apparatus including a relay chamber to introduce a sample to a sample preparation device or an evaluation device, a sample conveyance chamber to convey the sample between a plurality of relay chambers, a manipulator to hold the sample in each chamber and a sample conveyance rod to convey the sample between the chambers, the sample conveyance apparatus being configured to enable precise and prompt evaluation of a thin film sample such as semiconductor while keeping the prepared state.

JP Patent Publication (Kokai) No. 2005-148003 A (Patent Document 4) describes the following technique. A sample fixed to a temperature variable mechanism (heat insulation unit) of a sample stage is introduced to a sample chamber and the sample in a cooled state at a temperature lower than a room temperature is processed with an ion beam. Then, a sample chamber side and a vacuum line are separated while maintaining an ion beam generator and a detector under high vacuum using a shutter, followed by leakage of dry gas such as nitrogen and inert gas into the sample chamber, and a cover in the sample chamber is placed on the sample together with the heat insulation unit. Then the sample stage with the sample residing thereon is taken out from the sample chamber while placing the cover thereon in the atmosphere inside the cover controlled with a gas inlet unit.

JP Patent Publication (Kokai) No. 2000-21583 A (Patent Document 5) describes a sample holder capable of shielding the atmosphere and introducing gas into an airtight chamber. This sample holder is configured to move a sample holding unit between a forward end position where the sample holding unit projects from a sample holding unit projection exit (during sample observation) and a backward end position where the sample holding unit is placed in the airtight chamber. The sample holder further includes piping for letting in/out gas to/from the airtight chamber.

JP Patent Publication (Kokai) No. 2003-187735 A (Patent Document 6) describes a sample holder configured to hermetically seal a sample in a special atmosphere. This sample holder includes a diaphragm to separate a sample placing part from the interior of a sample chamber (vacuum) and a gas inlet tube leading to a sample placing space that is formed by the diaphragm.

Software to analyze a three-dimensional structure obtained by a TEM or the like also is available (Non Patent Document 1). Specifying a special part of a certain three-dimensional structure, such software is configured to display the distance between two points, the surface area, the volume, the density and the like of the specified part.

CITATION LIST

Patent Document 1: JP Patent Publication (Kokai) No. 2009-122122 A
Patent Document 2: JP Patent Publication (Kokai) No. 2007-188905 A
Patent Document 3: JP Patent Publication (Kokai) No. 06-349928 A (1994)
Patent Document 4: JP Patent Publication (Kokai) No. 2005-148003 A
Patent Document 5: JP Patent Publication (Kokai) No. 2000-215837 A
Patent Document 6: JP Patent Publication (Kokai) No. 2003-187735 A
Non Patent Document 1: "amira", "online", Visage Imaging, searched on Sep. 28, 2009, the Internet <URL:http://www.amiravis.com/overview.html>

DISCLOSURE OF THE INVENTION

Problem to be Solved by the Invention

As a result of keen examination on three-dimensional structure analysis of a sample using an electron microscope, the present inventors found the followings.

Currently materials relating to environmental energy such as materials for organic EL devices, lithium ion batteries, exhaust gas catalyst and the like are being developed quickly and so there is a growing demand for three-dimensional analysis of such materials.

Organic EL devices and lithium ion batteries, however, have the problem of readily reacting with atmosphere and water. Therefore the three-dimensional analysis therefor must be devised not to expose a sample to the atmosphere during conveyance from a sample preparation device to an observation device.

Exhaust gas catalyst is produced or used under gaseous atmosphere or on heating, a change in the material, e.g., a change of the surface area of catalyst particles has to be clearly captured in such environment.

Neither of the sample holders described in the aforementioned Patent Document 1 nor Patent Document 2 is devised not to expose a sample to the atmosphere. They are not devised for observation of a change of the sample due to the gas flow into/out of the airtight chamber, heating and light irradiation of the sample, either. In order to convey these sample holders without being exposed to the atmosphere, a glove box has to be used and the sample holder as a whole in the glove box has to be manipulated, which means very complicated manipulation. In order to form gaseous atmosphere, the glove box accommodating the sample holder as a whole has to be filled with gas inefficiently.

Although the sample conveyance apparatuses described in the aforementioned Patent Documents 3 and 4 are devised to deal with a sample in bulk, they are not devised to observe a three-dimensional structure of a sample.

The sample holder described in the aforementioned Patent Document 5 is not devised to implement three-dimensional analysis of a sample while holding the sample rotatably 360 degrees, e.g., observation from all directions and observation of an element distribution image. This sample holder is not devised for observation of a change in the sample due to heating or light irradiation, either.

The sample holder described in the aforementioned Patent Document 6 is not devised to implement three-dimensional analysis of a sample while holding the sample rotatably 360 degrees nor for observation of a change in the sample due to light irradiation, either.

It is an object of the invention to capture a change in a sample due to gaseous atmosphere, light irradiation, heating or the like without exposing the sample to the atmosphere.

Solution to the Problem

The present invention relates to a sample holder provided with a sample stage that is rotatable around a rotation axis perpendicular to an electron beam irradiation direction, the sample holder being capable of forming an airtight chamber around the sample stage.

Advantageous Effects of the Invention

According to the present invention, a sample can chemically react in any atmosphere and three-dimensional analysis on the reaction is enabled. Further, a sample liable to change in the atmosphere can be three-dimensionally analyzed without being exposed to the atmosphere.

DESCRIPTION OF EMBODIMENTS

Figure 1:
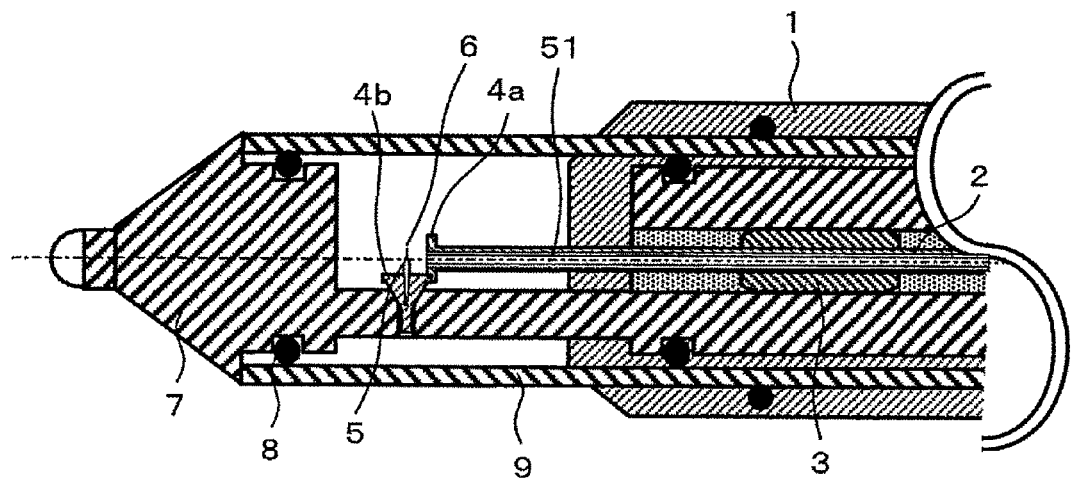
FIG. 1 is a cross-sectional view of a sample holder forward end in Embodiment 1.

One embodiment discloses a charged particle radiation apparatus including: a sample holder including a sample stage to hold a sample; an electron gun to generate an electron beam to be applied to the sample; a detector to detect an electron beam passing through the sample; a processor to perform operation processing of a transmission image that the detector acquires; and a display to display an operation result by the processor. In the apparatus, the sample holder includes a rotation mechanism having a rotation axis perpendicular to an irradiation direction of the electron beam, the rotation mechanism being capable of rotating the sample stage around the rotation axis 180 degrees, and a shielding mechanism capable of forming an airtight chamber around the sample stage, and the display displays three-dimensional information that is obtained by operation processing of a transmission image group obtained by rotating the sample stage by predetermined angles.

One embodiment discloses a method for displaying three-dimensional information in a charged particle radiation apparatus. The method includes the steps of: mounting a sample holder in a charged particle radiation apparatus, the sample holder including a shielding mechanism capable of forming an airtight chamber around a sample stage to hold a sample; rotating the sample stage by a rotation mechanism around a rotation axis perpendicular to an irradiation direction of an electron beam by a predetermined angle, irradiating the sample with an electron beam and detecting an electron beam passing through the sample; forming an airtight chamber around the sample stage by the shielding mechanism; making the airtight chamber in an open state, and thereafter rotating the sample stage around the rotation axis perpendicular to the irradiation direction of an electron beam by the rotation mechanism by a predetermined angle, irradiating the sample with an electron beam, and detecting an electron beam passing through the sample; performing, by a processor, operating processing device, operation processing of a transmission image group that a detector acquires; and displaying, by a display, a comparison result between first three-dimensional information and second three-dimensional information, the first three-dimensional information being obtained by rotating the sample stage by a predetermined angle and the second three-dimensional information being obtained by rotating the sample stage by a predetermined angle. One example discloses a display that displays a comparison result between first three-dimensional information and second three-dimensional information, the first three-dimensional information being obtained by rotating the sample stage by a predetermined angle and the second three-dimensional information being obtained by rotating the sample stage by a predetermined angle.

One embodiment discloses a method for displaying three-dimensional information in a charged particle radiation apparatus. The method includes the steps of: mounting a sample holder in an ion beam apparatus, the sample holder including a shielding mechanism capable of forming an airtight chamber around a sample stage to hold a sample; irradiating the sample with an ion beam to process the sample; forming an airtight chamber around the sample stage by the shielding mechanism; mounting the sample holder including the airtight chamber formed therein in a charged particle radiation apparatus; making the airtight chamber in an open state, and thereafter rotating the sample stage around a rotation axis perpendicular to an irradiation direction of an electron beam by a rotation mechanism by a predetermined angle, irradiating the sample with an electron beam, and detecting an electron beam passing through the sample; performing, by a processor, operation processing of a group of transmission images obtained; and displaying, by a display, three-dimensional information obtained by rotating the sample stage by a predetermined angle. One embodiment discloses a sample holder that is mountable to an ion beam apparatus.

In one embodiment disclosed, the display displays a comparison result of three-dimensional shapes.

In one embodiment disclosed, the display displays a comparison result of a surface area at any area selected from the three-dimensional information.

In one embodiment disclosed, the display displays a comparison result of a volume at any area selected from the three-dimensional information.

In one embodiment of a charged particle radiation apparatus disclosed, the sample holder includes gas piping capable of emitting gas in the airtight chamber formed by the shielding mechanism, and the display displays a comparison result between first three-dimensional information and second three-dimensional information, the first three-dimensional information being obtained by rotating the sample stage by a predetermined angle and the second three-dimensional information being obtained by, after gas emission, rotating the sample stage by a predetermined angle. In one embodiment of a method for displaying three-dimensional information disclosed, gas piping emits gas in the airtight chamber formed by the shielding mechanism, and the display displays a comparison result between first three-dimensional information and second three-dimensional information, the first three-dimensional information being obtained by rotating the sample stage by a predetermined angle and the second three-dimensional information being obtained by, after gas emission, rotating the sample stage by a predetermined angle.

In one embodiment of a charged particle radiation apparatus disclosed, the sample holder includes gas piping capable of emitting gas to a sample held to the sample stage, and the display displays a comparison result between first three-dimensional information and second three-dimensional information, the first three-dimensional information being obtained by rotating the sample stage by a predetermined angle and the second three-dimensional information being obtained by, after gas emission, rotating the sample stage by a predetermined angle. In one embodiment of a method for displaying three-dimensional information disclosed, gas piping emits gas in the airtight chamber formed by the shielding mechanism, and the display displays a comparison result between first three-dimensional information and second three-dimensional information, the first three-dimensional information being obtained by rotating the sample stage by a predetermined angle and the second three-dimensional information being obtained by, after gas emission, rotating the sample stage by a predetermined angle.

In one embodiment of a charged particle radiation apparatus disclosed, the sample holder includes gas piping capable of emitting electromagnetic waves to a sample held to the sample stage, and the display displays a comparison result between first three-dimensional information and second three-dimensional information, the first three-dimensional information being obtained by rotating the sample stage by a predetermined angle and the second three-dimensional information being obtained by, after gas emission, rotating the sample stage by a predetermined angle. In one embodiment of a method for displaying three-dimensional information disclosed, gas piping emits gas in the airtight chamber formed by the shielding mechanism, and the display displays a comparison result between first three-dimensional information and second three-dimensional information, the first three-dimensional information being obtained by rotating the sample stage by a predetermined angle and the second three-dimensional information being obtained by, after gas emission, rotating the sample stage by a predetermined angle.

In one embodiment disclosed, the shielding mechanism includes a covering unit to cover a forward end part of a supporting rod at the sample holder, and the shielding mechanism forms the airtight chamber as the covering unit moves.

In one embodiment disclosed, the shielding mechanism includes a mechanism to slide a supporting rod of the sample holder, and the shielding mechanism forms the airtight chamber by storing a forward end part of the supporting rod in a syringe of the sample holder.

The following describes the aforementioned and other new features and advantageous effects, with reference to the attached drawings. Note here that the drawings are used only for the understanding of the invention, and are not intended to limit the scope of the invention. The following embodiments can be combined appropriately, and the present specification is intended to disclose such a combined embodiment.

Embodiment 1

Figure 2:
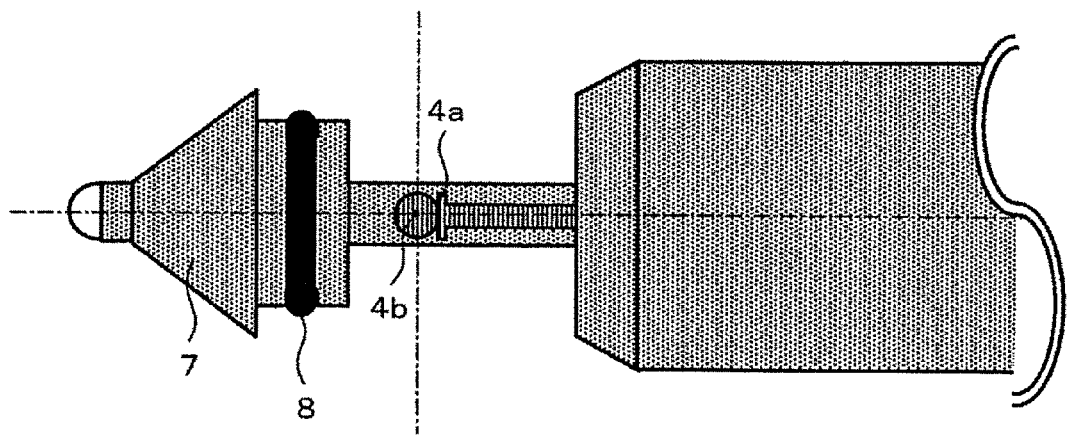
FIG. 2 is a top view of the sample holder forward end in Embodiment 1 (open state).
Figure 3:
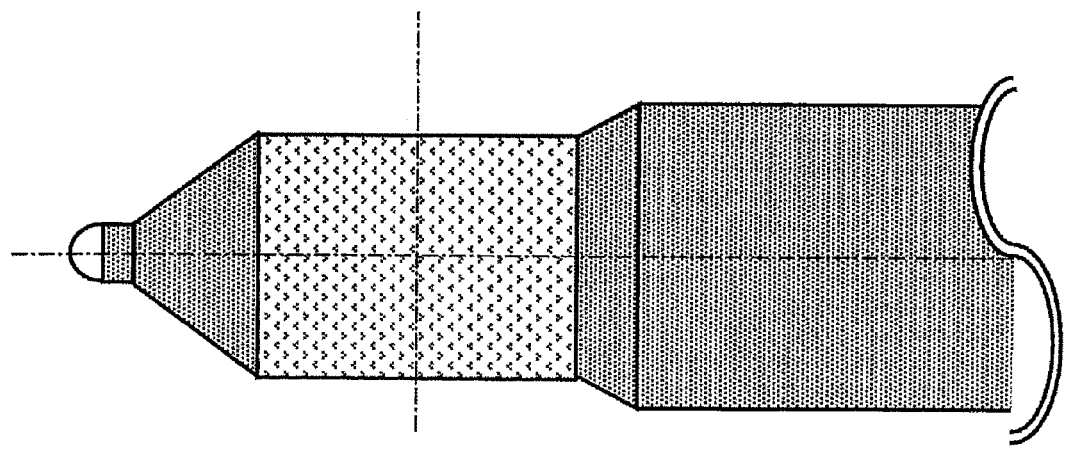
FIG. 3 is a top view of the sample holder forward end in Embodiment 1 (closed state).

FIG. 1 is a cross-sectional view of a sample holder forward end part of the present embodiment. FIG. 2 and FIG. 3 are top views of the sample holder forward end part of the present embodiment. A sample holder 1 includes a rotary shaft 2 attached at a forward end part thereof to be in parallel with a center axis of the sample holder. The rotary shaft 2 is held at a center position by a shaft holding part 3. The rotary shaft 2 includes a gear 4a attached at a forward end thereof. The gear 4a engages a gear 4b attached to a sample supporting rod 7. The gear 4b has a rotation axis perpendicular to a rotation axis of the gear 4a. The gear 4b has a hole bored at a center thereof. In this hole is inserted a needle-shaped sample stage 5 in a Morse taper shape and having a flat part at a forward end thereof. The sample 6 is fixed to a forward end part of the needle-shaped sample stage 5. The sample 6 may be a minute sample extracted from a base material using a focused ion beam and a probe. The sample 6 is fixed to the sample stage 5 by FIB assist deposition, for example.

As the rotary shaft 2 rotates with the rotation of a motor 14, the rotation is transmitted from the gear 4a to the gear 4b, thus rotating the sample stage 5 and the sample 6. In order to shield the rotation mechanism and the sample 6 at the forward end part of the sample holder 1 from outside air, a cylindrical covering unit 9 is provided so as to surround the sample supporting rod 7. The covering unit 9 can slide from a main body side of the sample holder 1 and is connectable with the sample supporting rod 7 via an O-ring 8. FIG. 1 and FIG. 3 illustrate a closed state of the covering unit 9 so as to shield the sample 6 or the like from outside air. FIG. 2 illustrates an open state of the covering unit 9 where the covering unit 9 is placed in the sample holder 1 so as to open the sample 6 or the like to the air.

The rotary shaft 2 provided at the center of the sample holder 1 has a hollow inside, and inside the rotary shaft 2 is provided gas piping 51 so as not to come into contact with the rotary shaft 2. The gas piping 51 has a gas outlet directed to the sample 6. The gas piping 51 has the other end connected to a gas feeding device. With this configuration, gas can be introduced in around the sample 6 while leaving the sample 6 in an airtight or an open state. Further, the sample 6 can be rotated while emitting gas thereto, the entire sample 6 can react with the gas uniformly. When the sample 6 is not rotated, differences of influence from gas can be checked in different positions.

Figure 4:
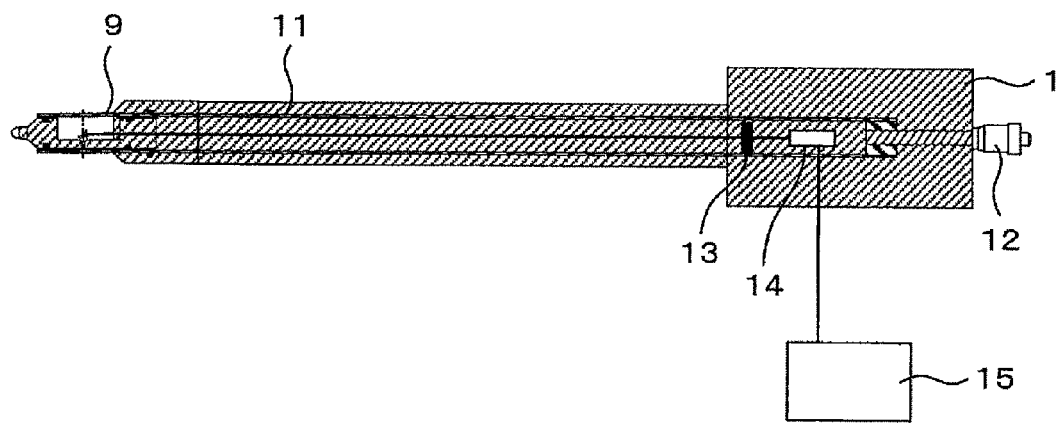
FIG. 4 is a cross-sectional view of the sample holder as a whole in Embodiment 1 (closed state).
Figure 5:
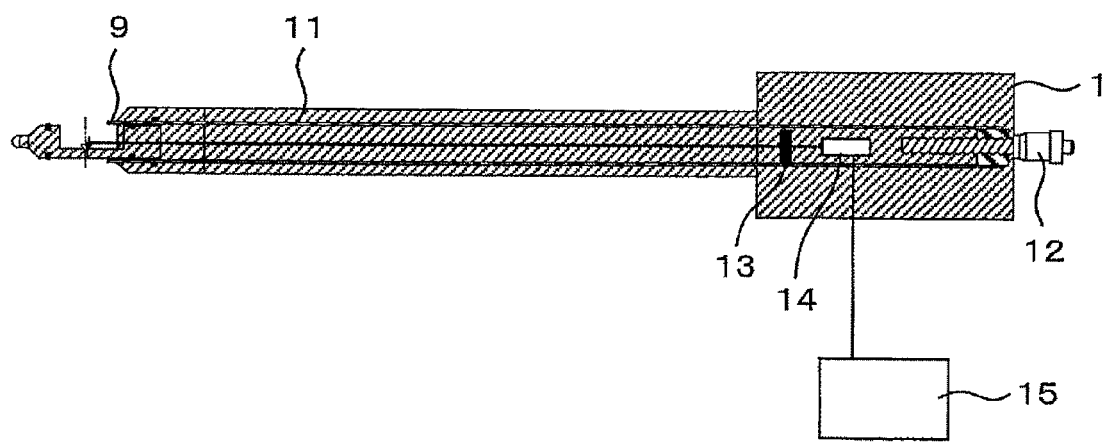
FIG. 5 is a cross-sectional view of the sample holder as a whole in Embodiment 1 (open state).

FIG. 4 and FIG. 5 are cross-sectional views of the sample holder 1 as a whole. FIG. 4 illustrates a closed state where the sample 6 is shielded from outside air. FIG. 5 is an open state where the sample 6 is opened to the air. These drawings omit the gas piping 51.

The covering unit 9 is attached to a covering unit driving unit 11, and the covering unit driving unit 11 is connected to a micrometer 12 located outside of a mirror body of the electron microscope, for example. The rotation of the micrometer 12 can move the covering unit driving unit 11 horizontally. The covering unit driving unit 11 is controlled so as to dispose the covering unit 9 at an electron beam passage portion, whereby the atmosphere around the sample 6 can be shielded from the outside. An end of the rotary shaft 2 is connected to the motor 14 outside of the vacuum via a hermetic seal 13. The motor 14 is connected to a motor power control unit 15.

Figure 6:
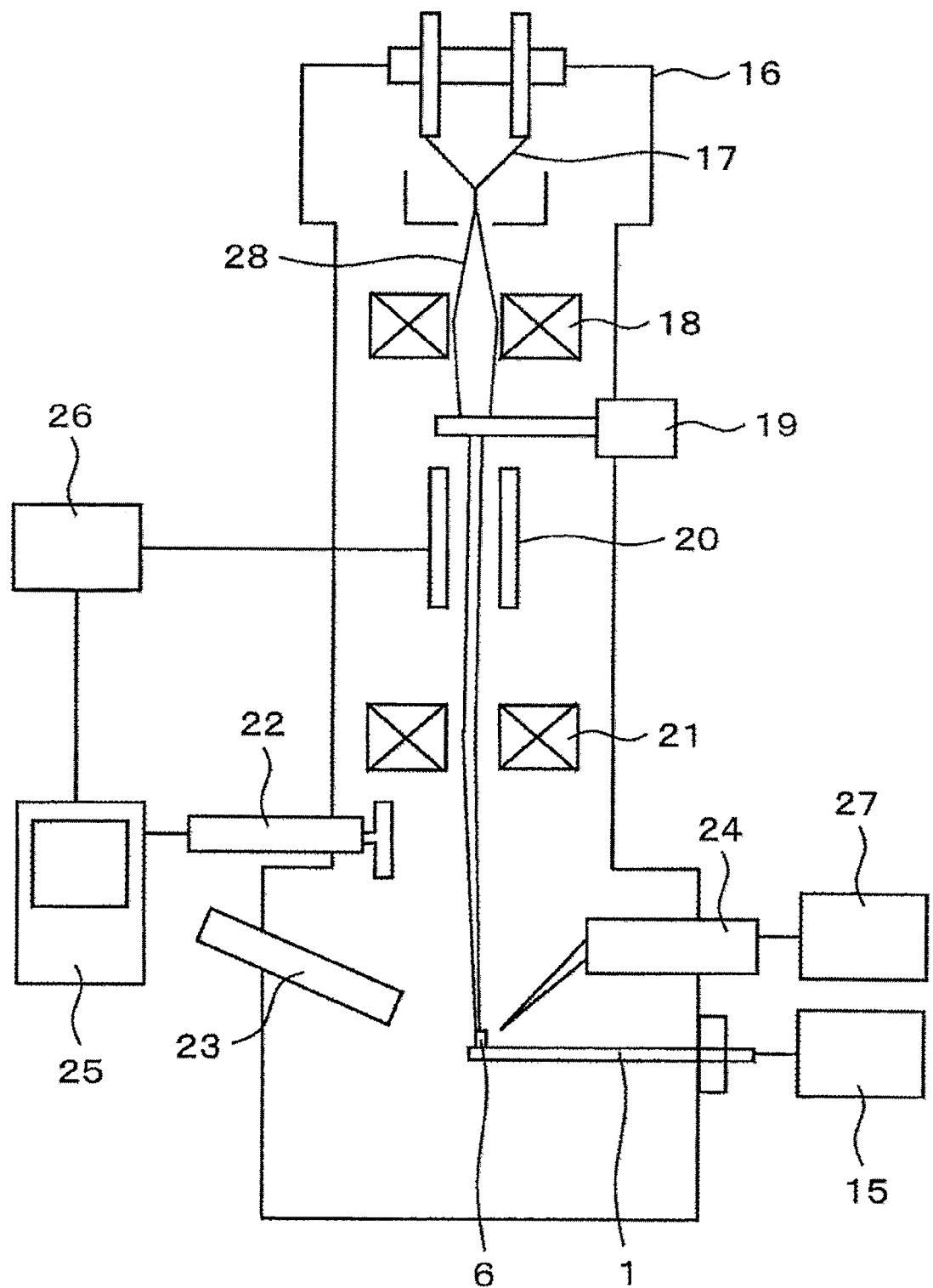
FIG. 6 schematically illustrates a configuration of a FIB processing apparatus used for sample preparation.

FIG. 6 schematically illustrates a configuration of a FIB apparatus 16 used for sample preparation. Inside a mirror body of the FIB apparatus 16 are disposed an ion gun 17, condenser lenses 18, a diaphragm 19, a scanning electrode 20 and object lenses 21. In the sample chamber of the FIB apparatus 16, the sample holder 1 with the sample 6 attached thereto is inserted. A loadlock system not illustrated is provided so as to enable removal and insertion of the sample holder 1 from/to the sample chamber while maintaining a vacuum state of the sample chamber. The sample holder 1 is connected to the motor power control unit 15. In FIG. 6, the covering unit 9 is in an open state, where the sample 6 can be irradiated with ion beams. Above the sample holder 1 is disposed a secondary electron detector 22. The secondary electron detector 22 is connected to a scan image display device 25. The scan image display device 25 is connected to the scanning electrode 20 via a scanning electrode control unit 26. The sample chamber is further provided with a deposition gum 23 for the purposes of forming a protective film of the sample 6 and fixing the sample 6 to the sample stage 5 and a microprobe 24 to convey the sample 6 extracted from a base material by FIB processing to the sample stage 5. The microprobe 24 is connected to a microprobe control device 27 to control a position of the microprobe 24.

An ion beam 28 emitted from the ion gun 17 converges via the condenser lenses 18 and the diaphragm 19, passes through the object lenses 21 and is applied on the sample 6. The scanning electrode 20 located above the object lenses 21 deflect and scan the ion beam 28 incident on the sample 6 in accordance with an instruction from the scanning electrode control unit 26. When the ion beam 28 is applied to the sample 6, a secondary electron is generated from the sample 6. The generated secondary electron is detected by the secondary electron detector 22, and is displayed as a sample image on the scan image display device 25. Based on the sample image, a processing area and a protective film formation area are decided. Herein, the processing area and the protective film formation area can be set by controlling a scanning area of the ion beam 28.

Gas emitted from the deposition gum 23 is decomposed by the applied ion beam 28, and metal included in the gas only is deposited at an applied area of the ion beam 28 on the face of sample 6 or the like. This deposited film may be used for the purposes such as protective film formation on the surface of the sample 6 before FIB processing, connection between the microprobe 24 and the sample 6 and fixing of the sample 6 conveyed by the microprobe 24 to the sample stage 5.

The sample 6 is prepared by cutting a desired portion of a base material with the ion beam 28, and is fixed at a tip end of the microprobe 24 by a deposited film formed by deposition. The sample holder 1 is mounted in the FIB apparatus 16 while leaving the covering unit 9 open. The sample 6 is conveyed by the microprobe 24 to the sample stage 5 provided at the forward end part of the sample holder 1, and the sample 6 is fixed to the sample stage 5 by deposition. After fixing of the sample 6, a connection part between the microprobe 24 and the sample 6 is disconnected by the ion beam 28. Thereafter, the sample 6 is processed by the ion beam 28 in a shape suitable for TEM or STEM observation. After processing, the vicinity of the sample 6 at the forward end part of the sample holder 1 is hermetically sealed by the covering unit 9 and the sample 6 is held in vacuum. In this state, the sample holder 1 is taken out from the FIB apparatus 16.

Figure 7:
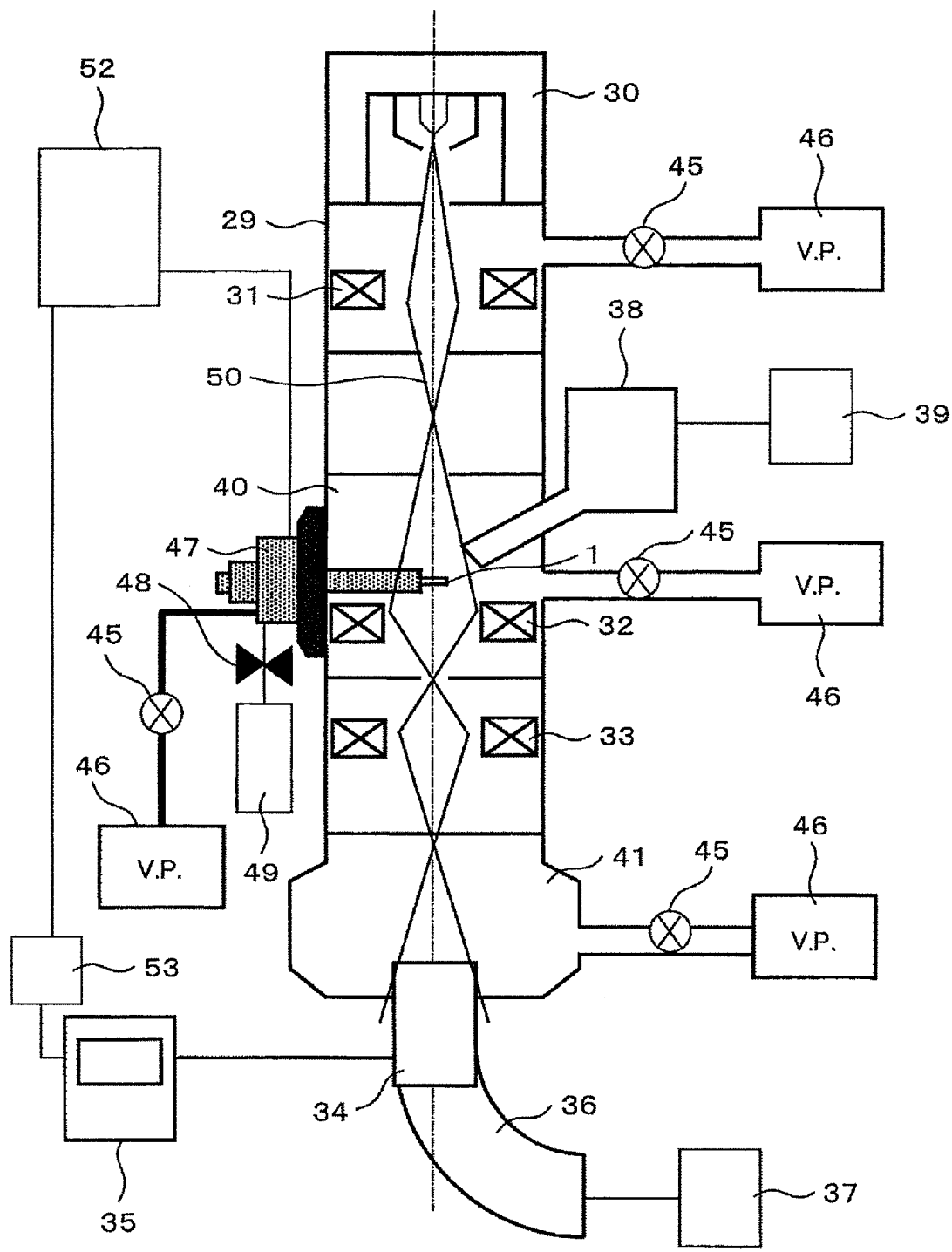
FIG. 7 schematically illustrates a configuration of an electron microscope used for three-dimensional analysis.

FIG. 7 illustrates a basic configuration of an electron microscope 29 used for three-dimensional analysis. Inside a mirror body of the electron microscope 29 are disposed an electron gun 30, condenser lenses 31, object lenses 32 and projection lenses 33, and the electron microscope 29 is connected to an electron microscope control device 52. Between the condenser lenses 31 and the object lenses 32 is inserted the sample holder 1. Below the projection lenses 33 is mounted a movable TV camera 34. The TV camera 34 is connected to an image display unit 35. The image display unit 35 is connected to an image recording unit 53. Below the TV camera 34 is attached an EELS detector 36, and the EELS detector 36 is connected to an EELS control unit 37. Above the sample holder 1 is provided an EDX detector 38, and the EDX detector 38 is connected to an EDX control unit 39. The image recording unit 53, the EELS control unit 37 and the EDX control unit 39 are connected to the electron microscope control device 52. The vicinity of the electron gun 30, the vicinity of the condenser lenses 31, a sample chamber 40 and an observation chamber 41 are connected to different vacuum pumps 46 via valves 45. Thereby, the interior of the electron microscope 29 is held in vacuum. A sample pre-evacuation chamber 47 also is connected to a vacuum pump 46 via a valve 45. Thereby, prior to introduction of the sample 6 to the sample chamber 40, pre-evacuation can be conducted. In order to enable gas introduction, a gas cylinder 49 further is installed via a valve 48.

The sample holder 1 taken out from the FIB apparatus 16 is inserted in the sample pre-evacuation chamber 47 of the electron microscope 29 while hermetically sealing the vicinity of the sample 6 by the covering unit 9. Inside the sample pre-evacuation chamber 47, the covering unit 9 is opened for pre-evacuation, and then the sample 6 is inserted into the sample chamber 40. In this way, the sample 6 can be conveyed from the FIB apparatus 16 to the interior of the electron microscope 29 without being exposed to the atmosphere.

An electron beam 50 generated from the electron gun 30 converges via the condenser lenses 31 and is applied to the sample 6. An image of the electron beam 50 passing through the sample 6 is formed by the object lenses 32, and is enlarged and projected by the projection lenses 33 on the TV camera 34. Thereby, a transmission image can be displayed on the image display unit 35.

The electron beam 50 can converge at one point on the sample 6 via the condenser lenses 31, whereby character X-rays from the area enters the EDX detector 38. In accordance with energy of the incident character X-rays, the EDX control unit 39 displays or analyzes a signal amount. Thereby, the sample 6 can be EDX-analyzed.

When the movable TV camera 34 is removed from the optical axis of the electron beam 50, the electron beam 50 passing through the sample 6, i.e., a transmission electron beam losing energy depending on the elements constituting the sample 6 and having various energy levels enters the EELS detector 36. The incident transmission electron beam on the EELS detector 36 is dispersed for each energy level, and is displayed and analyzed by the EELS control unit 37. Thereby, the sample 6 can EELS-analyzed.

The sample 6 can be rotated 360 degrees by the motor 14, and can be rotated by any angle for observation and analysis. Various images of the sample may be captured every few degrees, and then a three-dimensional image can be reconstructed from the captured images. The three-dimensional reconstruction enables calculation of the sample about a three-dimensional structure, a surface area, a density and a volume.

Figure 8:
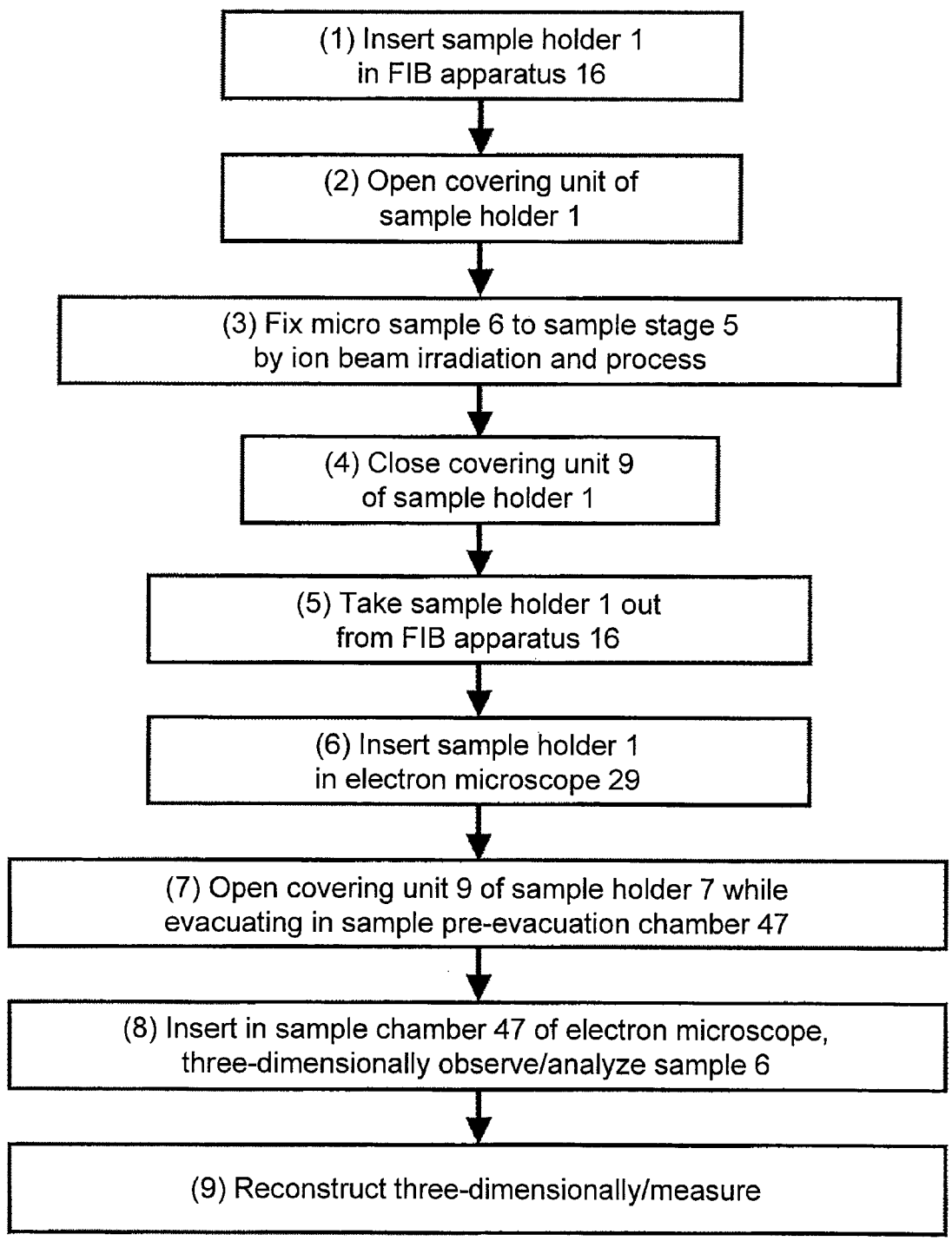
FIG. 8 illustrates the operation procedure in Embodiment 1.

FIG. 8 illustrates the procedure for three-dimensional analysis without exposing the sample 6 to the atmosphere.

(1) Firstly, the sample holder 1 is inserted in the FIB apparatus 16. More specifically, the sample holder 1 is inserted through an opening provided at a side wall of the sample chamber of the FIB apparatus 16. Thereby the sample holder 1 is fixed to the sample chamber so that a forward end part of the sample holder 1 is disposed on the optical axis of the ion beam 28. The sample stage 5 is set to be rotatable 360 degrees around the rotation axis in parallel with the optical axis of the ion beam 28, i.e., the rotation axis perpendicular to the installation plane of the FIB apparatus.

(2) Next, inside the FIB apparatus 16, the covering unit 9 of the sample holder 1 is opened. More specifically, the covering unit driving unit 11 is horizontally moved by rotating the micrometer 12 so as to place the covering unit 9 inside the sample holder 1. Thereby, the sample 6 or the like is in an open state, so that the ion beam 28 can be applied to the sample 6.

(3) After making the sample holder 1 in an open state, the minute sample 6 is fixed to the sample stage 5 by ion beam irradiation and then is processed. More specifically, the microprobe control device is controlled so that the minute sample 6 extracted from a base material using the sample ion beam 28 and the microprobe 24 is conveyed to the sample stage 5 attached to the forward end part of the holder 1. Thereafter the ion beam 28 is applied to the sample 6 while emitting gas from the deposition gum 23, whereby a deposition film is formed to fix the minute sample 6 to the sample stage 5. Then, the ion beam 28 is applied to the minute sample 6 fixed to the sample stage 5, thus processing the sample 6 into a shape suitable for observation using a transmission electron microscope. At this time, the ion beam 28 is applied while rotating the sample stage 5 by a desired angle under the control of the motor power control unit 15, whereby the minute sample 5 can be easily processed in a shape suitable for three-dimensional structure observation.

(4) After ion beam processing, the covering unit 9 of the sample holder 1 is closed. More specifically, the micrometer 12 is reverse-rotated from (3) so that the covering unit driving unit 11 is horizontally moved to slide the covering unit 9 to the outside of the sample holder 1. Thereby, the sample holder 1 assumes a closed state and the sample 6 is vacuum-sealed.

(5) After making the sample holder 1 in a closed state, the sample holder 1 is taken out from the FIB apparatus 16. More specifically, the sample holder 1 is pulled out from the sample chamber. Thereby, the sample holder 1 can be conveyed to an apparatus other than the FIB apparatus 16, e.g., to the electron microscope 29.

(6) The sample holder 1 is inserted in the electron microscope 29. More specifically, the sample holder 1 in a closed state is inserted in the sample pre-evacuation chamber 47. Thereby, pre-evacuation is enabled.

(7) Next, the covering unit 9 of the sample holder 1 is opened while conducting evacuation in the sample pre-evacuation chamber 47. More specifically, the valve 45 is opened, and the vacuum pump 46 is activated. Then, after the sample pre-evacuation chamber 47 reaches a vacuum state, the micrometer 12 is rotated so that the covering unit driving unit 11 is horizontal moved to place the covering unit 9 inside the sample holder 1. Thereby, the sample 6 processed for three-dimensional structure observation by the FIB apparatus 16 can be conveyed to the sample chamber 40 of the electron microscope 29 without being exposed to the atmosphere.

(8) After pre-evacuation, the sample 6 is inserted in the sample chamber 40 of the electron microscope, and three-dimensional observation and analysis of the sample 6 is executed. More specifically, after pre-evacuation, the sample holder 1 is further inserted. Thereby, the sample holder 1 is fixed to the sample chamber 40 so that the forward end part of the sample holder 1 is disposed on the optical axis of the electron beam 50, whereby the electron beam 50 can be applied to the sample 6. The sample stage 5 is set to be rotatable 360 degrees around the rotation axis perpendicular to the optical axis of the electron beam 50, i.e., the rotation axis in parallel with the installation plane of the electron microscope 29. Herein assume that the rotation angle of the sample stage 5 in this state is 0 degree. This information is transmitted from the motor power control unit 15 to the electron microscope control device 52 and is displayed on the image display unit 35.

The electron beam 50 accelerated by the electron gun 30 undergoes adjustment of the irradiation area by the condenser lenses 31, and is applied to the sample 6. After passing through the sample 6, a transmission image of the electron beam 50 is formed by the object lenses 32, is enlarged by the projection lenses 33 and is projected on the TV camera 34. Image data transmitted from the TV camera 34 to the control unit is recorded on the image recording unit 53 together with the rotation angle transferred from the motor power control unit. The image display unit 35 displays the rotation angle as well as the image data.

After recording on the image recording unit 53, the electron microscope control device 52 sends a signal indicating recording finish to the motor power control unit 15. Receiving this signal, the motor power control unit 15 controls the motor 14 to rotate the sample stage 5 by a predetermined angle. This predetermined angle is an angle step for photography while rotating the sample stage 5 by this predetermined angle, which may be 1 degree, 2 degrees or 5 degrees, for example. This angle may be set beforehand at the motor power control unit 15.

Then, this operation, i.e., acquisition of a transmission electron image and the rotation of the sample stage 5 is repeatedly performed until the rotation angle of the sample stage 5 reaches 180 degrees. This rotation angle 180 degrees of the sample stage 5 in the present embodiment may be 360 degrees, for example, as long as sufficient transmission images can be captured to reconstruct a three-dimensional structure.

(9) Using the transmission electron beam images photographed during rotation, a three-dimensional structure is reconstructed, and based on the structure, a volume, a surface area and the like are measured. The three-dimensional structure can be reconstructed by transferring images to a PC for three-dimension reconstruction connected to the image recording unit. More specifically, a set of data including the captured transmission images and the sample stage angles is transferred to the PC for three-dimension reconstruction. The PC for three-dimension image reconstruction uses software for three-dimension reconstruction to reconstruct a three-dimensional structure from the data set. For instance, Fourier transform is performed to a graph representing density values of a certain cross section of a captured image, and the resultants are overlaid to create a graph for frequency area. Fourier transform is further performed to the created graph, whereby a certain cross section is reconstructed. This operation is conducted at every position of the captured image, whereby a three-dimensionally reconstructed image can be obtained. From the three-dimensional image once reconstructed, any part is extracted, and a distance between two points, a volume, a surface area and the like are measured.

In the present embodiment, a transmission image at each rotation angle is captured for three-dimensional reconstruction. Instead, the EDX detector may be used and three-dimensional reconstruction may be conducted by the EDX control unit. In this case, for instance, an electron beam is narrowed thin on the sample face using the condenser lenses and is scanned. Then, the generated X-rays are detected by the EDX detector. Using a data set of the thus obtained component distribution images and the sample stage angles, three-dimensional reconstruction is performed by the EDX control unit.

Alternatively, the EELS detector may be used and three-dimensional reconstruction may be conducted by the EELS control unit. In this case, for instance, an electron beam is narrowed thin on the sample face using the condenser lenses and is scanned. Then, energy loss electrons are detected by the EELS detector. Using a data set of the thus obtained component distribution images and the sample stage angles, three-dimensional reconstruction is performed by the EELS control unit.

In this way, according to the present embodiment, the sample holder 1 can be conveyed in the atmosphere while holding the sample 6 in vacuum. Accordingly, the sample 6 can be three-dimensionally analyzed without altering the quality thereof by the atmosphere.

Embodiment 2

The present embodiment describes three-dimensional analysis of a sample reacting with gas before and after the reaction. The following mainly describes a difference from Embodiment 1.

Figure 9:
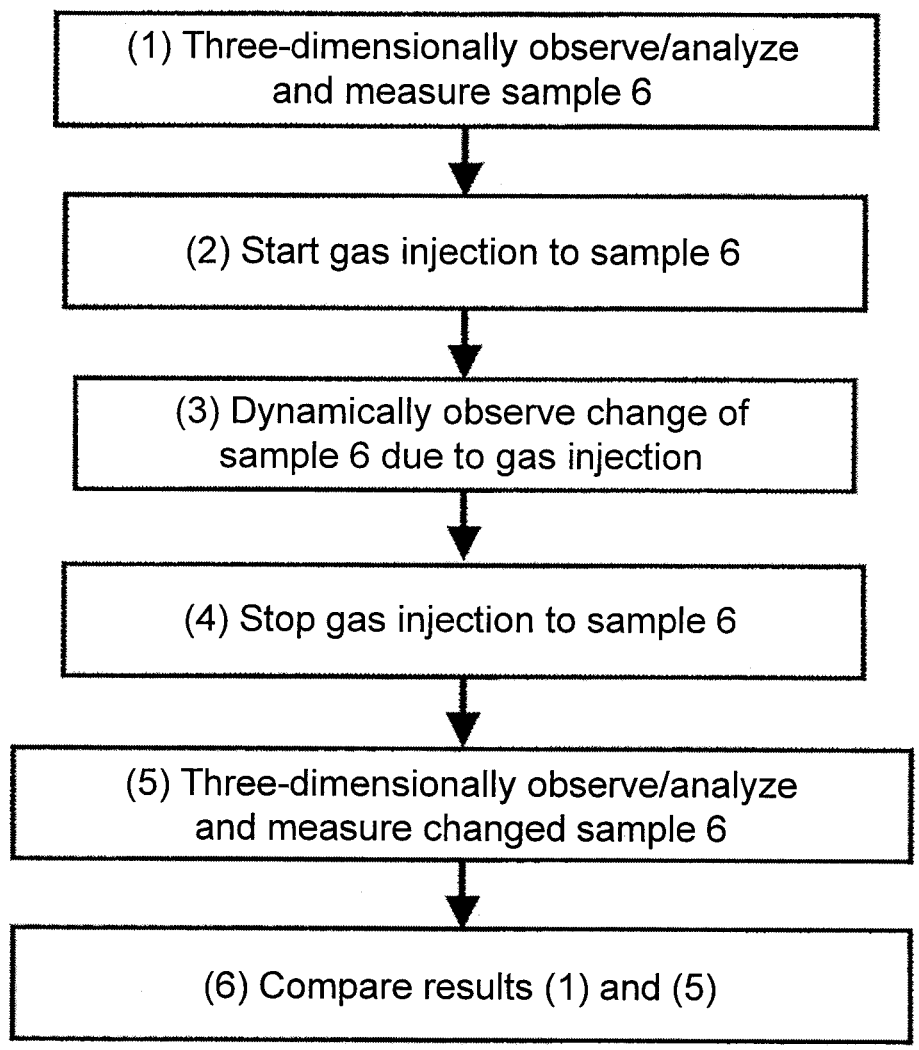
FIG. 9 illustrates the operation procedure in Embodiment 2.

FIG. 9 illustrates the procedure to explain an operation for three-dimensional analysis before and after gas reaction of the sample 6.

(1) With the procedure similar to (8) in Embodiment 1, the sample 6 is three-dimensionally observed and analyzed, and measured without exposing the sample 6 to the atmosphere.

(2) The valve 48 is adjusted so as to let the gas cylinder 49 emit a blast of gas with a desired pressure to the sample 6. When uniform reaction is required, the sample may be rotated under the control of the motor power control unit. When a change depending on the gas injection position is to be dynamically observed, the sample is not rotated.

(3) A change of the sample 6 due to gas injection is dynamically observed. Thereby, the state where catalyst particles gathers and unites in the gaseous atmosphere is observed, for example.

(4) The valve 48 is closed to stop gas injection to the sample 6. (5) With the procedure similar to (8) in Embodiment 1, the changed sample 6 is three-dimensionally observed and analyzed, and measurement thereof is performed.

(6) The results obtained in the procedure (1) and (5) are compared. More specifically, three-dimensional reconstruction images before and after the reaction are displayed. Alternatively, any part at the three-dimensional reconstruction image before the reaction or after the reaction is input to a PC for three-dimensional reconstruction, and the PC for three-dimensional reconstruction measures a change of a distance between two points, a volume, a surface area and the like before and after the reaction.

According to the present embodiment, the sample 6 undergoing gas injection can be three-dimensionally dynamically observed, and a change of the sample 6 before and after gas injection can be three-dimensionally analyzed. For instance, as for observation of fuel cell catalyst, the catalyst includes primary particles of a few microns in size that are carriers, on a surface of which rare metal particles of nanometer or less in size are dispersed. When such catalyst is exposed to gas, rare metal on the carriers moves and particles thereof grow. This particle growth of rare metals is considered as a factor to degrade the reactivity of the catalyst material because of a decrease in a surface area as an active surface. That is, degradation of catalyst can be analyzed by finding a change in the disperse state. For example, a change of a surface area of rare metal particles per unit volume of the carrier, a distance between rare metal catalyst particles and a change of a volume before and after gas reaction may be found based on three-dimensional reconstruction results. As a result, a change of the disperse state of the rare metal particles can be understood, whereby properties of the catalysts can be understood and degradation thereof can be analyzed.

Embodiment 3

The present embodiment describes three-dimensional analysis of a sample heated or light irradiated before and after such a treatment. The following mainly describes a difference from Embodiments 1 and 2.

In the present embodiment, instead of the gas piping 51, an optical fiber 51' is disposed. Thereby, the sample 6 is irradiated with light and a change thereof can be three-dimensionally analyzed. Further, a nanolaser, for example, can be incorporated at a light entrance directed to the sample 6, thus allowing the sample 6 to be irradiated with laser light and heated. The optical fiber 51' and the nanolaser may be provided together with the gas piping 51.

Figure 10:
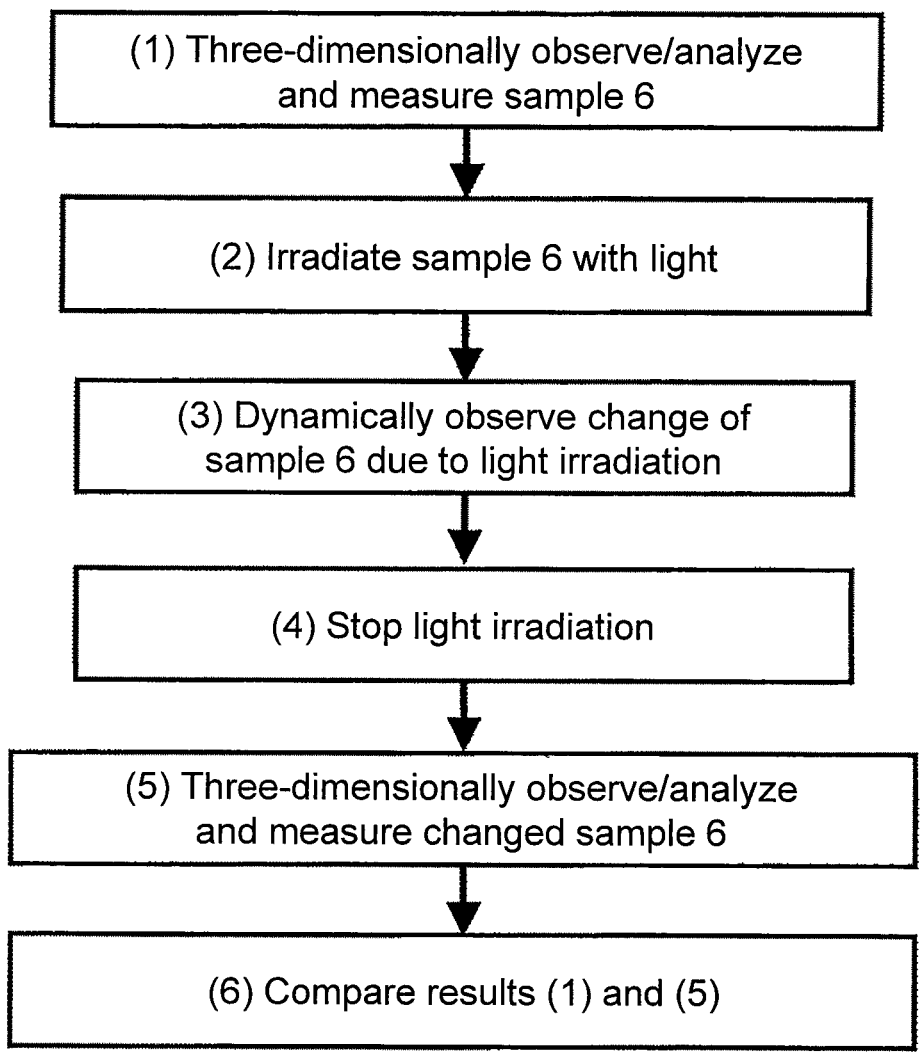
FIG. 10 illustrates the operation procedure in Embodiment 3.

FIG. 10 illustrates the operation procedure for three-dimensional analysis before and after heating of the sample 6.

(1) With the procedure similar to (8) in Embodiment 1, the sample 6 is three-dimensionally observed and analyzed, and measured without exposing the sample 6 to the atmosphere.

(2) The sample 6 is irradiated with light or laser. Depending on the purpose, the sample 6 is irradiated with light or laser while being rotated.

(3) A change of the sample 6 due to light or laser irradiation is dynamically observed.

(4) Light or laser irradiation to the sample 6 is stopped. (5) With the procedure similar to (8) in Embodiment 1, the changed sample 6 is three-dimensionally observed and analyzed, and measurement thereof is performed.

(6) The results obtained in the procedure (1) and (5) are compared.

According to the present embodiment, the sample 6 being irradiated with light or laser can be dynamically observed, and the sample 6 before and after light or laser irradiation can be three-dimensionally analyzed. The present embodiment can be expected as an application to photocatalyst analysis, for example. Irradiated with light (especially ultraviolet light), photocatalyst generates active oxygen, thus decomposing an organic compound to change the organic compound into water and carbon dioxide. Therefore, a change of a volume of the catalyst before and after light irradiation or a change of a volume of a mixed sample of catalyst and an organic compound is measured, for example, whereby the irradiation amount and the change amount can be understood. Further, the process of the change can be observed at the atomic level.

Although the present embodiment assumes the irradiation with ultraviolet rays and YAG laser, electromagnetic waves such as infrared rays and visual light may be applied depending on the analysis purposes.

Embodiment 4

The present embodiment describes three-dimensional analysis before and after high-temperature gas reaction. The present embodiment further describes a sample holder capable of accommodating a sample stage inside thereof. The following mainly describes a difference from Embodiments 1 to 3.

In the present embodiment, a gas inlet system is provided in the sample pre-evacuation chamber 47 of the electron microscope 29 in Embodiment 1.

Figure 11:
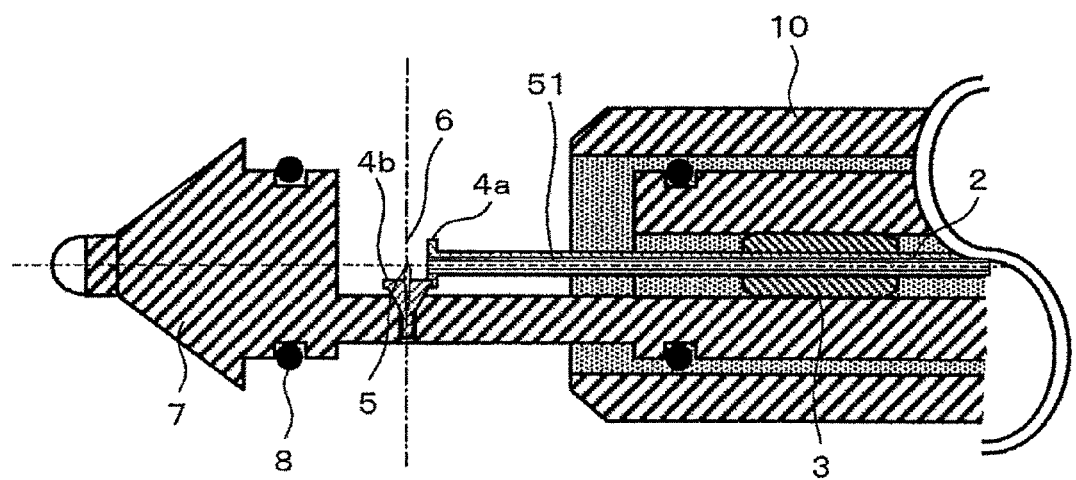
FIG. 11 is a cross-sectional view of a sample holder forward end in Embodiment 4.
Figure 12:
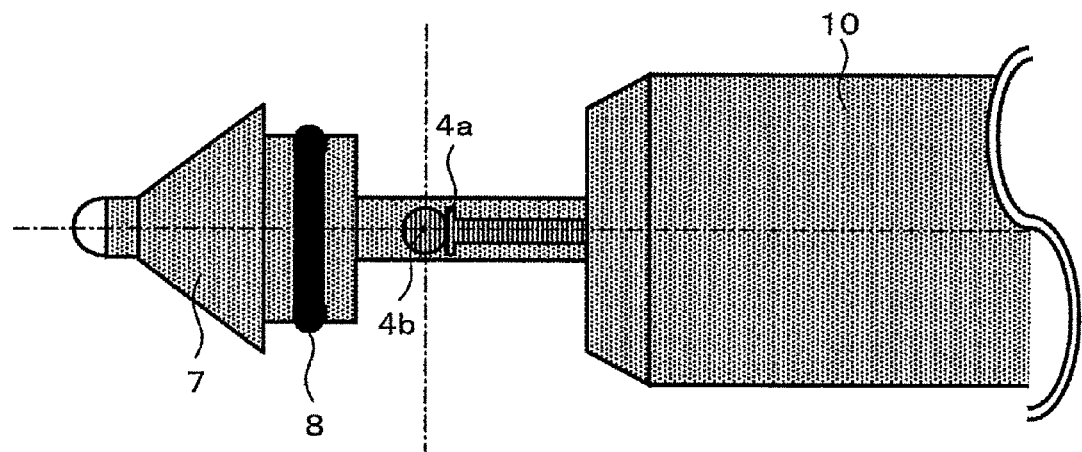
FIG. 12 is a top view of the sample holder forward end in Embodiment 4 (open state).
Figure 13:
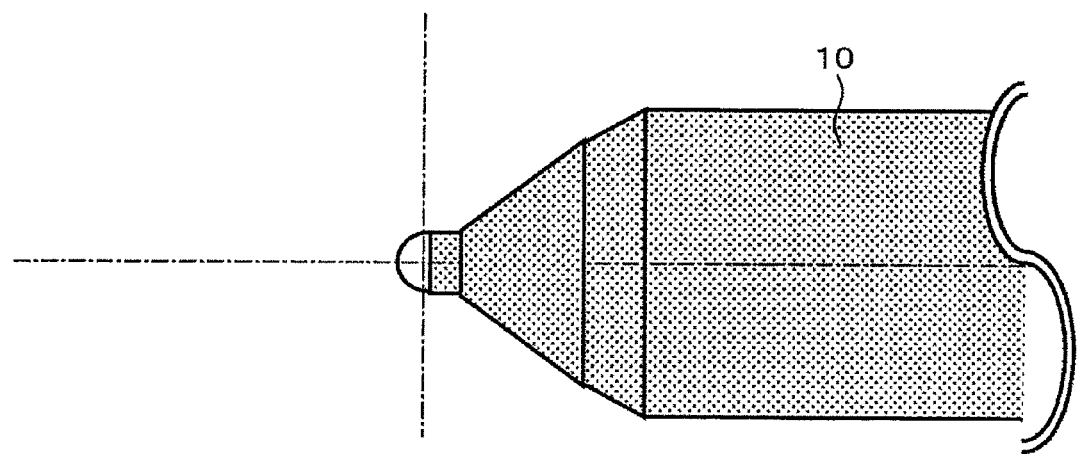
FIG. 13 is a top view of the sample holder forward end in Embodiment 4 (closed state).

FIG. 11 is a cross-sectional view of a sample holder forward end part of the present embodiment. FIG. 12 and FIG. 13 are top views of the sample holder forward end, illustrating an open state and a closed state, respectively. The present embodiment has a sample rotation system similar to that in Embodiment 1. In order to shield the rotation mechanism and the sample 6 at the forward end part of the sample holder 1 from outside air, a sample supporting rod 7 can be slid and put inside of a cylinder 10. Sliding of the sample supporting rod 7 can be controlled from the main body side of the sample holder 1. FIG. 11 and FIG. 12 illustrate the open state where the sample supporting rod 7 protrudes from the sample holder 1 to let the sample 6 or the like open. FIG. 13 illustrates the closed state where the sample supporting rod 7 is stored inside of the cylinder 10 to shield the sample 6 or the like from outside air.

Figure 14:
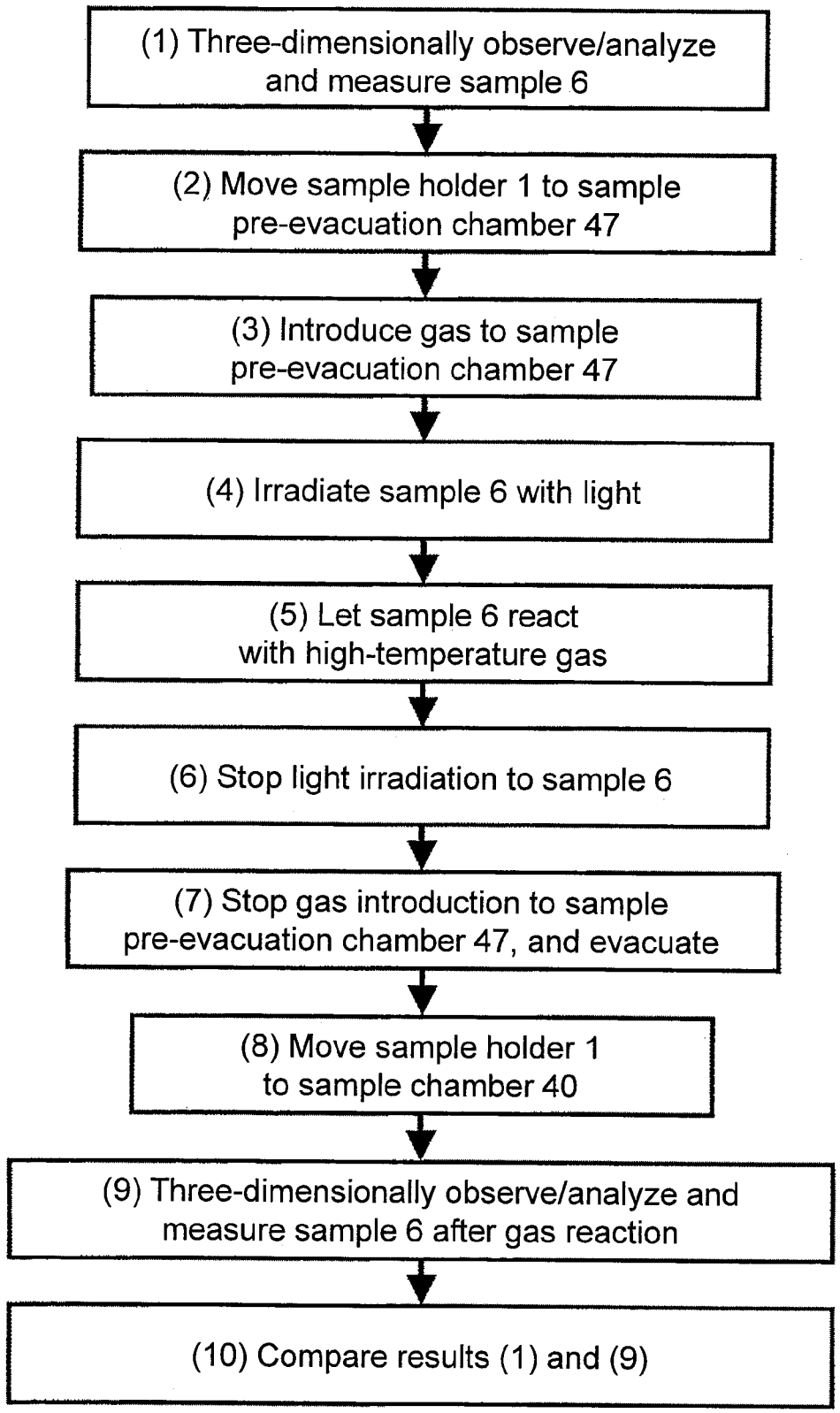
FIG. 14 illustrates the operation procedure in Embodiment 4.

FIG. 14 illustrates the procedure for three-dimensional analysis of the sample 6 before and after high-temperature gas reaction.

(1) With the procedure similar to (8) in Embodiment 1, the sample 6 is three-dimensionally observed and analyzed, and measured without exposing the sample 6 to the atmosphere.

(2) The sample holder 1 is moved to the sample pre-evacuation chamber 47 of the electron microscope 29 while leaving the forward end part of the sample holder 1 in a open state.

(3) Gas is introduced to the sample pre-evacuation chamber 47, and the sample 6 is irradiated with laser while rotating the sample 6, thus letting the sample 6 react with the gas at a high temperature. Laser irradiation is performed from a laser external to the electron microscope via an optical fiber. The output of the laser is controlled by a controller connected to the laser so that the temperature of the heated sample can be at a desired value.

(4) Gas introduction to the sample pre-evacuation chamber 47 and laser irradiation are stopped, and the sample pre-evacuation chamber 47 is evacuated.

(5) The sample holder 1 is moved to the sample chamber 40 while leaving the forward end part of the sample holder 1 in an open state.

(6) With the procedure similar to (8) in Embodiment 1, the sample 6 after high-temperature gas reaction is three-dimensionally observed and analyzed, and measurement thereof is performed.

(7) The results obtained in the procedure (1) and (6) are compared. Thereby the sample 6 before and after high-temperature gas reaction can be three-dimensionally analyzed.

In the present embodiment, the sample reacts with high temperature gas in the sample pre-evacuation chamber 47. Alternatively, a gas inlet nozzle may be provided in a sample storage unit in addition to the optical fiber, whereby the sample can react with high temperature gas inside the sample chamber while leaving the sample storage unit in the closed state. In this case, the interior of the storage unit is evacuated, and then the forward end part of the sample holder 1 is opened, and the sample after reaction is three-dimensionally observed and analyzed, and measured.

For example, exposed to exhaust gas catalyst at high temperatures, rare metal as a carrier moves and the particle thereof grow. Therefore, a change of a disperse state of these rare metal particles has to be understood. According to the present embodiment, a change of a surface area of the rare metal particles per unit volume of the carrier, a change among rare metal catalyst particles and a change of a volume of the rare metal particles before and after high temperature gas reaction can be found. As a result, properties of the catalyst can be understood and degradation thereof can be analyzed.

INDUSTRIAL APPLICABILITY

The present invention enables precise three-dimensional analysis on environmental energy related materials such as evaluation of organic EL devices and lithium ion batteries that readily react with atmosphere and water and degradation analysis for exhaust gas catalyst. Since the present invention can produce various environmental conditions by combining reaction with light in gas, reaction in heat and the like, a broad range of applications can be expected in the field of material analysis.

DESCRIPTION OF REFERENCE NUMBERS

1 Sample holder
2 Rotary shaft
3 Shaft holding part
4 Gear
5 Sample stage
6 Sample
7 Sample supporting rod
8 O-ring
9 Covering unit
10 Cylinder
11 Covering unit driving unit
12 Micrometer
13 Hermetic seal
14 Motor
15 Motor power control unit
16 FIB apparatus
17 Ion gun
18 Condenser lenses
19 Diaphragm
20 Scanning electrode
21 Object lenses
22 Secondary electron detector
23 Deposition gum
24 Microprobe
25 Scan image display device
26 Scanning electrode control unit
27 Microprobe control device
28 Ion beam
29 Electron microscope
30 Electron gun
31 Condenser lenses
32 Object lenses
33 Projection lenses
34 TV camera
35 Image display unit
36 EELS detector
37 EELS control unit
38 EDX detector
39 EDX control unit
40 Sample chamber
41 Observation chamber
45, 48 Valve 46 Vacuum pump
47 Sample pre-evacuation chamber
49 Gas cylinder
50 Electron beam
51 Gas piping
52 Electron microscope control device
53 Image recording unit

The invention claimed is:

1. A charged particle radiation apparatus, comprising:
a sample holder including a sample stage to hold a sample;
a sample chamber to which the sample holder is inserted;
a gun to generate a charged particle beam to be applied to the sample;
a detector to detect a radiation from the sample; and
a processor to acquire an image from the radiation from the sample,
wherein the sample holder includes a rotation mechanism including a rotary shaft being capable of rotating the sample stage around a rotation axis by a predetermined angle, and a shielding mechanism capable of forming an airtight chamber around the sample stage, and
the charged particle radiation apparatus further comprising a piping to supply the sample with a medium which reacts to the sample, wherein at least a part of the piping is in the rotary shaft and the shielding mechanism;
wherein the processor acquires a first image before supplying the medium, a second image after supplying the medium, three dimensional information from the first image and the second image, and a distance between rare metal catalyst particles.

2. A method for displaying three-dimensional information in a charged particle radiation apparatus, comprising the steps of:
mounting a sample holder in a sample chamber of a charged particle radiation apparatus, the sample holder including a shielding mechanism capable of forming an airtight chamber around a sample stage to hold a sample;
rotating the sample stage by a rotation mechanism including a rotary shaft being capable of rotating the sample stage around a rotation axis by a predetermined angle,
irradiating the sample with an electron beam and detecting an electron beam passing through the sample;
forming an airtight chamber around the sample stage by the shielding mechanism; making the airtight chamber in an open state, and thereafter rotating the sample stage around the rotation axis by the rotation mechanism by the predetermined angle, irradiating the sample with the electron beam, and detecting an electron beam passing through the sample;
performing, by a processor, acquiring an image from radiation from the sample;
supplying, by a piping, the sample with a medium that reacts to the sample, wherein at least a part of the piping is in the rotary shaft and the shielding mechanism; and
acquiring a first image before supplying the medium, a second image after supplying the medium, three-dimensional information from the first image and the second image, and a distance between rare metal catalyst particles.

3. A method for displaying three-dimensional information in a charged particle radiation apparatus, comprising the steps of:
mounting a sample holder in a sample chamber of an ion beam apparatus, the sample holder including a shielding mechanism capable of forming an airtight chamber around a sample stage to hold a sample;
irradiating the sample with an ion beam to process the sample; forming an airtight chamber around the sample stage by the shielding mechanism;
mounting the sample holder including the airtight chamber formed therein in a charged particle radiation apparatus;
making the airtight chamber in an open state, and thereafter rotating the sample stage around a rotation axis by a rotation mechanism including a rotary shaft by a predetermined angle, irradiating the sample with an electron beam, and detecting an electron beam passing through the sample;
performing, by a processor, acquiring an image from radiation from the sample; and
supplying, by a piping, the sample with a medium that reacts to the sample, wherein at least a part of the piping is in the rotary shaft and the shielding mechanism;
wherein the processor acquires a first image before supplying the medium, a second image after supplying the medium, three dimensional information from the first image and the second image, and a distance between rare metal catalyst particles.

4. The charged particle radiation apparatus according to claim 1, wherein the rotation mechanism does not rotate the sample, when a change depending on a medium injection position is to be dynamically observed.

5. The charged particle radiation apparatus according to claim 1, wherein the rotation axis is substantially perpendicular to an optical axis of the charged particle beam.

6. The charged particle radiation apparatus according to claim 1, further comprising:
a display to display an operation result by the processor;
wherein the display displays three-dimensional information that is obtained by operation processing of a transmission image group obtained by rotating the sample stage by predetermined angles.

7. The charged particle radiation apparatus according to claim 6, wherein
the display displays a comparison result between first three-dimensional information and second three-dimensional information, the first three-dimensional information being obtained by rotating the sample stage by a predetermined angle and the second three- dimensional information being obtained by rotating the sample stage by a predetermined angle.

8. The charged particle radiation apparatus according to claim 7, wherein the display displays a comparison result of three-dimensional shapes.

9. The charged particle radiation apparatus according to claim 7, wherein the display displays a comparison result of a surface area at any area selected from the three-dimensional information.

10. The method for displaying three-dimensional information according to claim 2, wherein the rotation mechanism does not rotate the sample, when a change depending on a medium injection position is to be dynamically observed.

11. The method for displaying three-dimensional information according to claim 2, wherein the rotation axis is substantially perpendicular to an optical axis of the charged particle beam.

12. The method for displaying three-dimensional information according to claim 2, further comprising:
displaying, by a display, three-dimensional information that is obtained by operation processing of a transmission image group obtained by rotating the sample stage by predetermined angles.

13. The method for displaying three-dimensional information according to claim 12, wherein the display displays a comparison result of three-dimensional shapes.

14. The method for displaying three-dimensional information according to claim 12, wherein the display displays a comparison result of a surface area at any area selected from the three-dimensional information.

15. The method for displaying three-dimensional information according to claim 3, wherein the shielding mechanism includes a covering unit to cover a forward end part of a supporting rod at the sample holder, and the shielding mechanism forms the airtight chamber as the covering unit moves.

16. The method for displaying three-dimensional information according to claim 3, wherein the shielding mechanism includes a mechanism to slide a supporting rod of the sample holder, and the shielding mechanism forms the airtight chamber by storing a forward end part of the supporting rod in a syringe of the sample holder.

17. The charged particle radiation apparatus according to claim 7, wherein the display displays a comparison result of a volume at any area selected from the three-dimensional information.

18. The charged particle radiation apparatus according to claim 6, wherein the medium is a gas, and the piping supplies the airtight chamber formed by the shielding mechanism with the gas, and the display displays a comparison result between first three-dimensional information and second three-dimensional information, the first three-dimensional information being obtained by rotating the sample stage by a predetermined angle and the second three- dimensional information being obtained by, after gas emission, rotating the sample stage by a predetermined angle.

19. The charged particle radiation apparatus according to claim 6, wherein the medium is a gas, and the piping supplies the sample held to the sample stage with the gas, and
the display displays a comparison result between first three-dimensional information and second three-dimensional information, the first three-dimensional information being obtained by rotating the sample stage by a predetermined angle and the second three- dimensional information being obtained by, after gas emission, rotating the sample stage by a predetermined angle.

20. The charged particle radiation apparatus according to claim 6, wherein the sample holder includes a fiber cable capable of emitting electromagnetic waves to a sample held to the sample stage, and
the display displays a comparison result between first three-dimensional information and second three-dimensional information, the first three-dimensional information being obtained by rotating the sample stage by a predetermined angle and the second three- dimensional information being obtained by, after gas emission, rotating the sample stage by a predetermined angle.

21. The charged particle radiation apparatus according to claim 6, wherein the shielding mechanism includes a covering unit to cover a forward end part of a supporting rod at the sample holder, and the shielding mechanism forms the airtight chamber as the covering unit moves.

22. The charged particle radiation apparatus according to claim 6, wherein the shielding mechanism includes a mechanism to slide a supporting rod of the sample holder, and the shielding mechanism forms the airtight chamber by storing a forward end part of the supporting rod in a syringe of the sample holder.

23. The charged particle radiation apparatus according to claim 6, wherein the sample holder is mountable to an ion beam apparatus.

24. The method for displaying three-dimensional information according to claim 12, wherein the display displays a comparison result of a volume at any area selected from the three-dimensional information.

25. The method for displaying three-dimensional information according to claim 12, wherein the medium is a gas, and the piping supplies the airtight chamber formed by the shielding mechanism with the gas, and
the display displays a comparison result between first three-dimensional information and second three-dimensional information, the first three-dimensional information being obtained by rotating the sample stage by a predetermined angle and the second three-dimensional information being obtained by, after gas emission, rotating the sample stage by a predetermined angle.

26. The method for displaying three-dimensional information according to claim 12, wherein
the medium is a gas, and the piping supplies the sample held to the sample stage with the gas, and
the display displays a comparison result between first three-dimensional information and second three-dimensional information, the first three-dimensional information being obtained by rotating the sample stage by a predetermined angle and the second three-dimensional information being obtained by, after gas emission, rotating the sample stage by a predetermined angle.

27. The method for displaying three-dimensional information according to claim 12, wherein the shielding mechanism includes a covering unit to cover a forward end part of a supporting rod at the sample holder, and the shielding mechanism forms the airtight chamber as the covering unit moves.

28. The method for displaying three-dimensional information according to claim 12, wherein the shielding mechanism includes a mechanism to slide a supporting rod of the sample holder, and the shielding mechanism forms the airtight chamber by storing a forward end part of the supporting rod in a syringe of the sample holder.

* * * * *